US011395696B2

United States Patent
Wang

(10) Patent No.: US 11,395,696 B2
(45) Date of Patent: Jul. 26, 2022

(54) RADIOFREQUENCY ABLATION PROBE WITH DIRECTIONAL COOLING FOR LESION SIZE CONTROL

(71) Applicant: Avent, Inc., Alpharetta, GA (US)

(72) Inventor: Ruoya Wang, Decatur, GA (US)

(73) Assignee: Avent, Inc., Alpharetta, GA (US)

( * ) Notice: Subject to any disclaimer, the term of this patent is extended or adjusted under 35 U.S.C. 154(b) by 623 days.

(21) Appl. No.: 16/233,233

(22) Filed: Dec. 27, 2018

(65) Prior Publication Data

US 2020/0205886 A1     Jul. 2, 2020

(51) Int. Cl.
*A61B 18/14* (2006.01)
*A61B 18/12* (2006.01)
*A61B 18/00* (2006.01)

(52) U.S. Cl.
CPC ...... *A61B 18/1492* (2013.01); *A61B 18/1206* (2013.01); *A61B 2018/00023* (2013.01); *A61B 2018/00083* (2013.01); *A61B 2018/00577* (2013.01); *A61B 2018/00702* (2013.01); *A61B 2018/00821* (2013.01); *A61B 2018/00827* (2013.01); *A61B 2018/00964* (2013.01); *A61B 2018/126* (2013.01);
(Continued)

(58) Field of Classification Search
CPC ... A61B 18/1492; A61B 18/148; A61B 18/14; A61B 2018/0022; A61B 2018/00285; A61B 2018/00023; A61B 2018/00214; A61B 2018/00005; A61B 2018/00011; A61B 2018/00744; A61B 2018/00702; A61B 2018/00791; A61B 2218/002; A61B 2218/005
USPC ....... 606/41, 42; 607/99, 101, 105, 115, 116
See application file for complete search history.

(56) References Cited

U.S. PATENT DOCUMENTS

| | | | |
|---|---|---|---|
| 9,393,070 B2* | 7/2016 | Gelfand | A61B 18/18 |
| 9,956,032 B1 | 5/2018 | Cosman et al. | |
| 2014/0081260 A1* | 3/2014 | Cosman, Jr. | A61B 18/14 |
| | | | 606/41 |

FOREIGN PATENT DOCUMENTS

| | | |
|---|---|---|
| EP | 1 001 495 B1 | 11/2005 |
| EP | 1 786 346 B1 | 3/2012 |

(Continued)

OTHER PUBLICATIONS

International Search Report and Written Opinion for PCT/US2019/067408, dated Mar. 27, 2020, 18 pages.

*Primary Examiner* — Thomas A Giuliani
(74) *Attorney, Agent, or Firm* — Meunier Carlin & Curfman LLC

(57) ABSTRACT

A cooled radiofrequency ablation system including a probe assembly having a proximal region, a distal tip region, and a shaft is provided. First and second internal cooling fluid tubes extend from the proximal region and are positioned inside a cavity defined by the shaft. The distal tip region includes a conductive portion for delivering energy to a target location within tissue. The system also includes a radiofrequency generator for delivering energy to the target location and a cooling fluid reservoir and a bidirectional pump assembly for circulating a cooling fluid from the reservoir through the first internal cooling fluid tube then the second internal cooling fluid tube when the pump operates in a first direction or through the second internal cooling fluid tube then the first internal cooling fluid tube when the pump operates in a second direction to form lesions of different sizes at the target location.

15 Claims, 7 Drawing Sheets

(52) U.S. Cl.
CPC ............... *A61B 2018/1253* (2013.01); *A61B 2018/1427* (2013.01); *A61B 2018/1432* (2013.01)

(56) References Cited

FOREIGN PATENT DOCUMENTS

| | | |
|---|---|---|
| JP | H 10314210 A | 12/1998 |
| WO | WO 96/34571 A1 | 11/1996 |
| WO | WO 2006/021095 A1 | 3/2006 |
| WO | WO 2011/134080 A1 | 11/2011 |

\* cited by examiner

RADIOFREQUENCY ABLATION PROBE WITH DIRECTIONAL COOLING FOR LESION SIZE CONTROL

FIELD OF THE INVENTION

The present invention relates generally to a probe for applying energy for the treatment of tissue, for example in a radiofrequency (RF) ablation procedure.

BACKGROUND

Lower back injuries and chronic joint pain are major health problems resulting not only in debilitating conditions for the patient, but also in the consumption of a large proportion of funds allocated for health care, social assistance and disability programs. In the lower back, disc abnormalities and pain may result from trauma, repetitive use in the workplace, metabolic disorders, inherited proclivity, and/or aging. The existence of adjacent nerve structures and innervation of the disc are very important issues in respect to patient treatment for back pain. In joints, osteoarthritis is the most common form of arthritis pain and occurs when the protective cartilage on the ends of bones wears down over time.

A minimally invasive technique of delivering high-frequency electrical current has been shown to relieve localized pain in many patients. Generally, the high-frequency current used for such procedures is in the radiofrequency (RF) range, i.e. between 100 kHz and 1 GHz and more specifically between 300-600 kHz. The treatment of pain using high-frequency electrical current has been applied successfully to various regions of patients' bodies suspected of contributing to chronic pain sensations. In addition to creating lesions in neural structures, application of radiofrequency energy has also been used to treat tumors throughout the body.

The RF electrical current is typically delivered from a generator via connected electrodes that are placed in a patient's body, in a region of tissue that contains a neural structure suspected of transmitting pain signals to the brain. The electrodes generally include one of more probes defining an insulated shaft with an exposed conductive active electrode tip to deliver the radiofrequency electrical current. Tissue resistance to the current causes heating of tissue adjacent resulting in the coagulation of cells (at a temperature of approximately 45° C. for small unmyelinated nerve structures) and the formation of a lesion that effectively denervates the neural structure in question. Denervation refers to affecting a neural structure's ability to transmit signals and usually results in the complete inability of a neural structure to transmit signals, thus removing the pain sensations.

To extend the size of a lesion, radiofrequency treatment may be applied in conjunction with a cooling mechanism, whereby a cooling means is used to reduce the temperature of the tissue near an energy delivery device, allowing a higher voltage to be applied without causing an unwanted increase in local tissue temperature. The application of a higher voltage allows regions of tissue further away from the energy delivery device to reach a temperature at which a lesion can form, thus increasing the size/volume of the lesion compared to conventional (non-cooling) radiofrequency treatments, where the larger size/volume of the lesion can increase the probability of success of ablating a target nerve. Cooled radiofrequency ablation is achieved by delivering, in a closed-loop circulation, cooling fluid (e.g., sterile water) via a peristaltic pump through the probe/active electrode. The cooling fluid continuously transfers heat away from the active electrode, allowing the electrode-tissue interface temperature to be maintained at a level that does not char or significantly dessicate the surrounding tissue, which is the primary limitation of conventional radiofrequency ablation. As a result, more radiofrequency energy can be delivered to the tissue, creating a lesion having a larger volume/size compared to a lesion created by conventional radiofrequency ablation.

Currently, the only way to control the lesion size is by changing the active electrode tip length at a distal end of the probe used to deliver the radiofrequency energy. A user can select active tip lengths in increments of 2 millimeters, 4 millimeters, 4 millimeters, 5.5 millimeters, and 6 millimeters depending on the local anatomy, where a longer active electrode tip results in a larger lesion. However, there are several disadvantages to controlling the lesion size based on active electrode tip lengths. For instance, the user must have additional inventory on hand to support multiple active tip lengths, certain anatomies may require multiple lesions of different sizes, which requires the use of multiple active electrode tip length probes, and it may be difficult for users to differentiate the active electrode tip lengths due to their small size.

Thus, a new and improved cooled radiofrequency ablation probe, system and method that addresses the issues noted above would be welcomed in the art.

SUMMARY OF THE INVENTION

Objects and advantages of the invention will be set forth in part in the following description, or may be obvious from the description, or may be learned through practice of the invention.

According to one particular embodiment of the present invention, a cooled radiofrequency ablation system is contemplated. The system includes a probe assembly comprising a proximal region; a hollow elongated shaft defining an internal cavity, wherein a first internal cooling fluid tube and a second internal cooling fluid tube are positioned inside the internal cavity and extend from the proximal region; and a distal tip region comprising a conductive portion for delivering energy to a target location within tissue; a radiofrequency generator for delivering energy to the target location via the conductive portion of the distal tip region of the probe assembly; and a cooling device including a cooling fluid reservoir and a bidirectional pump assembly operable to circulate a cooling fluid from the cooling fluid reservoir through the first internal cooling fluid tube, the internal cavity, the second internal cooling fluid tube, and back to the cooling fluid reservoir when the bidirectional pump is operating in a first direction, or from the cooling fluid reservoir through the second internal cooling fluid tube, the internal cavity, the first internal cooling fluid tube, and back to the cooling fluid reservoir when the bidirectional pump is operating in a second direction.

In one embodiment, the first internal cooling fluid tube can have a length that is less than a length of the second internal cooling fluid tube. For instance, the length of the first internal cooling fluid tube can be less than about 40% of the length of the second internal cooling fluid tube, such as from about 5% to about 35% of the length of the second internal cooling fluid tube. Further, a larger lesion can be formed at the target location when the bidirectional pump is operating in the second direction compared to when the bidirectional pump is operating in the first direction.

In another embodiment, the bidirectional pump assembly can be located upstream from the cooling fluid reservoir in the first direction and downstream from the cooling fluid reservoir in the second direction, or the bidirectional pump assembly can be located downstream from the cooling fluid reservoir in the first direction and upstream from the cooling fluid reservoir in the second direction.

In still another embodiment, the radiofrequency generator can include a user input for selecting a lesion size.

In yet another embodiment, the system can include an introducer that has a proximal end having a hub and a cannula extending from the hub that has a distal end. Further, the system can include a stylet that is insertable through the hub and into the cannula of the introducer, wherein the stylet can include a tissue-piercing distal end that extends from the distal end of the cannula when the stylet is inserted into the introducer. In addition, the introducer can electrically insulate the proximal region of the probe assembly when the probe assembly is inserted into the cannula.

According to another particular embodiment of the present invention, a method for delivering cooled radiofrequency energy to a target location within tissue via a probe assembly to form a lesion is contemplated. The method includes positioning a distal tip region of the probe assembly near the target location, wherein the distal tip region includes a conductive portion for delivering energy to the target location, wherein the probe assembly also comprises a proximal region and a hollow elongated shaft defining an internal cavity, wherein a first internal cooling fluid tube and a second internal cooling fluid tube are positioned inside the internal cavity and extend from the proximal region; selecting a lesion size via a user input located on a radiofrequency generator; delivering radiofrequency energy from the radiofrequency generator to the conductive portion of the distal tip region; and delivering cooling fluid to the distal tip region via a cooling device including a cooling fluid reservoir and a bidirectional pump assembly, wherein the bidirectional pump assembly circulates the cooling fluid from the cooling fluid reservoir through the first internal cooling fluid tube, the internal cavity, the second internal cooling fluid tube, and back to the cooling fluid reservoir when the bidirectional pump is operating in a first direction, or from the cooling fluid reservoir through the second internal cooling fluid tube, the internal cavity, the first internal cooling fluid tube, and back to the cooling fluid reservoir when the bidirectional pump is operating in a second direction depending on the lesion size selected.

In one embodiment, the first internal cooling fluid tube can have a length that is less than a length of the second internal cooling fluid tube. For instance, the length of the first internal cooling fluid tube can be less than about 40% of the length of the second internal cooling fluid tube, such as from about 5% to about 35% of the length of the second internal cooling fluid tube.

In another embodiment, a larger lesion can be formed at the target location when the bidirectional pump is operating in the second direction compared to when the bidirectional pump is operating in the first direction.

In still another embodiment, the bidirectional pump assembly can be located upstream from the cooling fluid reservoir in the first direction and downstream from the cooling fluid reservoir in the second direction, or the bidirectional pump assembly can be located downstream from the cooling fluid reservoir in the first direction and upstream from the cooling fluid reservoir in the second direction.

In yet another embodiment, the user input can be a graphical user interface.

According to another particular embodiment of the present invention, a cooled radiofrequency ablation probe assembly for delivering energy to a target location within tissue is contemplated. The probe assembly includes a proximal region; a hollow elongated shaft defining an internal cavity, wherein a first internal cooling fluid tube and a second internal cooling fluid tube are positioned inside the internal cavity and extend from the proximal region, wherein the first internal cooling fluid tube has a length that is less than a length of the second internal cooling fluid tube; and a distal tip region including a conductive portion for delivering energy to the target location.

In one embodiment, the length of the first internal cooling fluid tube can be less than about 40% of the length of the second internal cooling fluid tube. For instance, the length of the first internal cooling fluid tube can be from about 5% to about 35% of the length of the second internal cooling fluid tube.

In another embodiment, a larger lesion can be formed at the target location tissue when cooling fluid enters the cooled radiofrequency ablation probe assembly via the second internal cooling fluid tube compared to when cooling fluid enters the cooled radiofrequency ablation probe assembly via the first internal cooling fluid probe.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION OF THE INVENTION

Figure 1:
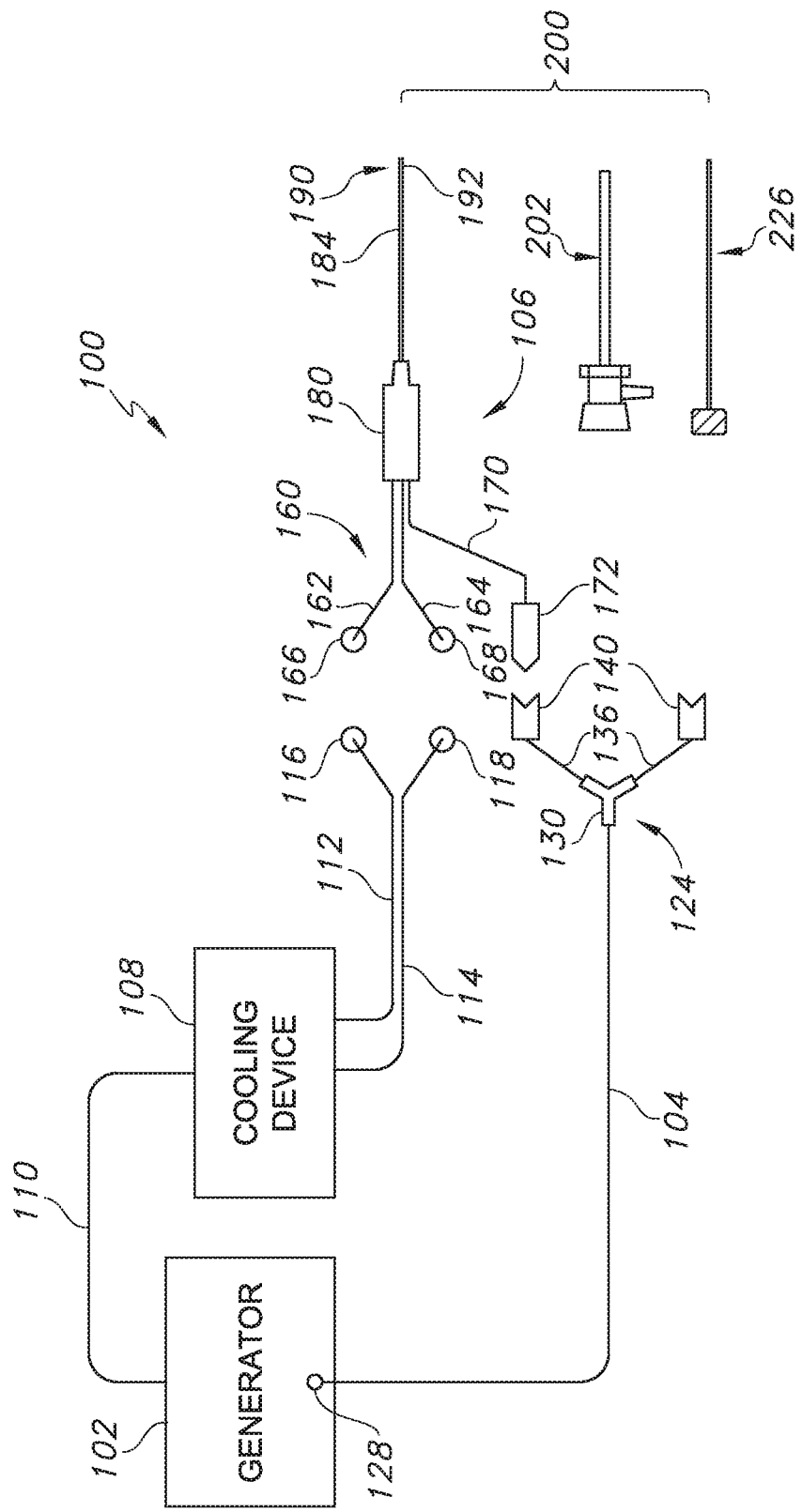
FIG. 1 is a diagram of a system for applying cooled radiofrequency (RF) electrical energy to target tissue in a patient's body, including a probe assembly and one or more cooling devices.

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention. Further, as used herein, the term "about," when used to modify a value, indicates that the value can be raised or lowered by 0.5% and remain within the disclosed embodiment.

Before explaining various embodiments of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

For the purposes of this invention, a lesion refers to any effect achieved through the application of energy to a tissue in a patient's body, and the invention is not intended to be limited in this regard. Furthermore, for the purposes of this description, proximal generally indicates that portion of a device or system next to or nearer to a user (when the device is in use), while the term distal generally indicates a portion further away from the user (when the device is in use).

Generally speaking, the present invention is directed to a cooled radiofrequency ablation system. The system includes a probe assembly having a proximal region, a distal tip region, and a hollow elongated shaft. The hollow elongated shaft defines an internal cavity, and a first internal cooling fluid tube and a second internal cooling fluid tube are positioned inside the internal cavity and extend from the proximal region. Further, the distal tip region includes a conductive portion for delivering energy to a target location within tissue. The system also includes a radiofrequency generator for delivering energy to the target location within tissue via the conductive portion of the distal tip region of the probe assembly, as well as a cooling device including a cooling fluid reservoir and a bidirectional pump assembly operable to circulate a cooling fluid from the cooling fluid reservoir through the first internal cooling fluid tube, the internal cavity, the second internal cooling fluid tube, and back to the cooling fluid reservoir when the bidirectional pump is operating in a first direction; or from the cooling fluid reservoir through the second internal cooling fluid tube, the internal cavity, the first internal cooling fluid tube, and back to the cooling fluid reservoir when the bidirectional pump is operating in a second direction. The various features of the cooled radiofrequency ablation system will now be discussed in more detail in reference to FIGS. 1-8.

Turning first to FIG. 1, a schematic diagram of an energy delivery system 100 for the delivery of energy, such as RF energy, to a target location within tissue of a patient is provided, and is presented herein for purposes of describing an exemplary operating environment in which the present introducer and assembly may be used. The system 100 includes a generator 102, a cable 104, one or more probe assemblies 106 (only one probe assembly is shown), one or more cooling devices 108 that include a one or more cooling fluid reservoirs 109 and a bidirectional pump assembly 120 (see FIGS. 6-7), a pump cable 110, one or more proximal cooling fluid supply tubes 112, and one or more proximal cooling fluid return tubes 114. The generator 102 may be a radiofrequency (RF) generator, or any other energy source, such as microwave energy, thermal energy, ultrasound, or optical energy. The generator 102 may include a display that displays various aspects of a treatment procedure, such as any parameters that are relevant to a treatment procedure, for example temperature, impedance, etc. and errors or warnings related to a treatment procedure. Alternatively, the generator 102 may include means of transmitting a signal to an external display. The generator 102 is operable to communicate with the first and second probe assemblies 106 and the one or more cooling devices 108. Such communication may be unidirectional or bidirectional depending on the devices used and the procedure performed.

In addition, as shown, a distal region 124 of the cable 104 may include a splitter 130 that divides the cable 104 into two distal ends 136 such that the probe assemblies 106 can be connected thereto. A proximal end 128 of the cable 104 is connected to the generator 102. This connection can be permanent, whereby, for example, the proximal end 128 of the cable 104 is embedded within the generator 102, or temporary, whereby, for example, the proximal end 128 of cable 104 is connected to generator 102 via an electrical connector. The two distal ends 136 of the cable 104 terminate in connectors 140 operable to couple to the probe assemblies 106 and establish an electrical connection between the probe assemblies 106 and the generator 102. In alternate embodiments, the system 100 may include a separate cable for each probe assembly 106 being used to couple the probe assemblies 106 to the generator 102.

The cooling device(s) 108 may include any means of reducing a temperature of material located at and proximate to one or more of the probe assemblies 106. For example, the cooling devices 108 may include a pump assembly 120, such as a bidirectional pump assembly, operable to circulate a fluid from the cooling devices 108 through one or more proximal cooling fluid supply tubes 112, the probe assemblies 106 (e.g., through an internal cavity 122 of the probe assemblies 106 (see FIGS. 4-7)), one or more proximal cooling fluid return tubes 114, and back to the one or more cooling devices 108.

The system 100 may include a controller for facilitating communication between the cooling devices 108 and the generator 102 via a feedback control loop. The feedback control may be implemented, for example, in a control module which may be a component of the generator 102. In such embodiments, the generator 102 is operable to communicate bidirectionally with the probe assemblies 106 as well as with the cooling devices 108, wherein bidirectional communication refers to the capability of a device to both receive a signal from and send a signal to another device.

As an example, the generator 102 may receive temperature measurements from one or both of the first and second probe assemblies 106. Based on the temperature measurements, the generator 102 may perform some action, such as modulating the power that is sent to the probe assemblies 106. Thus, both probe assemblies 106 may be individually controlled based on their respective temperature measurements.

The pumps associated with the cooling devices 108 may communicate a fluid flow rate to the generator 102 and may receive communications from the generator 102 instructing the pumps to modulate this flow rate. With the cooling devices 108 turned off, any temperature sensing elements associated with the probe assemblies 106 would not be affected by the cooling fluid allowing a more precise determination of the surrounding tissue temperature to be made. In addition, when using more than one probe assembly 106, the average temperature or a maximum temperature in the temperature sensing elements associated with probe assemblies 106 may be used to modulate cooling.

The cooling devices 108 may reduce the rate of cooling or disengage depending on the distance between the probe assemblies 106. For example, when the distance is small enough such that a sufficient current density exists in the region to achieve a desired temperature, little or no cooling may be required. In such an embodiment, energy is preferentially concentrated between first and second energy delivery devices 192 through a region of tissue to be treated, thereby creating a strip lesion characterized by an oblong volume of heated tissue that is formed when an active electrode is in close proximity to a return electrode of similar dimensions.

The cooling devices 108 may also communicate with the generator 102 to alert the generator 102 to one or more possible errors and/or anomalies associated with the cooling devices 108. For example, if cooling flow is impeded or if a lid of one or more of the cooling devices 108 is opened. The generator 102 may then act on the error signal by at least one of alerting a user, aborting the procedure, and modifying an action.

Still referring to FIG. 1, the proximal cooling fluid supply tubes 112 may include proximal supply tube connectors 116 at the distal ends of the one or more proximal cooling fluid supply tubes 112. Additionally, the proximal cooling fluid return tubes 114 may include proximal return tube connectors 118 at the distal ends of the one or more proximal cooling fluid return tubes 114. In one embodiment, the proximal supply tube connectors 116 are female luer-lock type connectors and the proximal return tube connectors 118 are male luer-lock type connectors although other connector types are intended to be within the scope of the present invention.

In addition, as shown in FIG. 1, the probe assembly 106 may include a proximal region 160, a handle 180, a hollow elongate shaft 184, which can also be referred to as an electrocap, and a distal tip region 190 that includes the one or more energy delivery devices 192 and that can also be referred to as the active tip. The elongate shaft 184 may be manufactured out of polyimide, which provides exceptional electrical insulation while maintaining sufficient flexibility and compactness. In alternate embodiments, the elongate shaft 184 may be any other material imparting similar qualities. In still other embodiments, the elongate shaft 184 may be manufactured from an electrically conductive material and may be covered by an insulating material so that delivered energy remains concentrated at the energy delivery device 192 of the distal tip region 190. The proximal region 160 includes a distal cooling fluid supply tube 162, a distal supply tube connector 166, a distal cooling fluid return tube 164, a distal return tube connector 168, a probe assembly cable 170, and a probe cable connector 172. In such embodiments, the distal cooling fluid supply tube 162 and distal cooling fluid return tube 164 are flexible to allow for greater maneuverability of the probe assemblies 106, but alternate embodiments with rigid tubes are possible.

The distal supply tube connector 166 may be a male luer-lock type connector and the distal return tube connector 168 may be a female luer-lock type connector. Thus, the proximal supply tube connector 116 may be operable to interlock with the distal supply tube connector 166 and the proximal return tube connector 118 may be operable to interlock with the distal return tube connector 168.

The probe cable connector 172 may be located at a proximal end of the probe assembly cable 170 and may be operable to reversibly couple to one of the connectors 140, thus establishing an electrical connection between the generator 102 and the probe assembly 106. The probe assembly cable 170 includes one or more conductors to transmit RF current from the generator 102 to the one or more energy delivery devices 192, as well as to connect multiple temperature sensing devices to the generator 102 as discussed below.

The energy delivery devices 192 may include any means of delivering energy to a region of tissue adjacent to the distal tip region 190. For example, the energy delivery devices 192 may include an ultrasonic device, an electrode or any other energy delivery means and the invention is not limited in this regard. Similarly, energy delivered via the energy delivery devices 192 may take several forms including but not limited to thermal energy, ultrasonic energy, radiofrequency energy, microwave energy or any other form of energy. For example, in one embodiment, the energy delivery devices 192 may include an electrode. The active region of the electrode may be 2 to 20 millimeters (mm) in length and energy delivered by the electrode is electrical energy in the form of current in the RF range. The size of the active region of the electrode can be optimized for placement within an intervertebral disc, however, different sizes of active regions, all of which are within the scope of the present invention, may be used depending on the specific procedure being performed. In some embodiments, feedback from the generator 102 may automatically adjust the exposed area of the energy delivery device 192 in response to a given measurement such as impedance or temperature. For example, in one embodiment, the energy delivery devices 192 may maximize energy delivered to the tissue by implementing at least one additional feedback control, such as a rising impedance value.

FIG. 1 also depicts an introducer 202 and a stylet 226, wherein the combination of the RF probe assembly 106, the introducer 202, and the stylet 226 define an RF ablation probe system 200 in accordance with aspects of the present invention.

Figure 2:
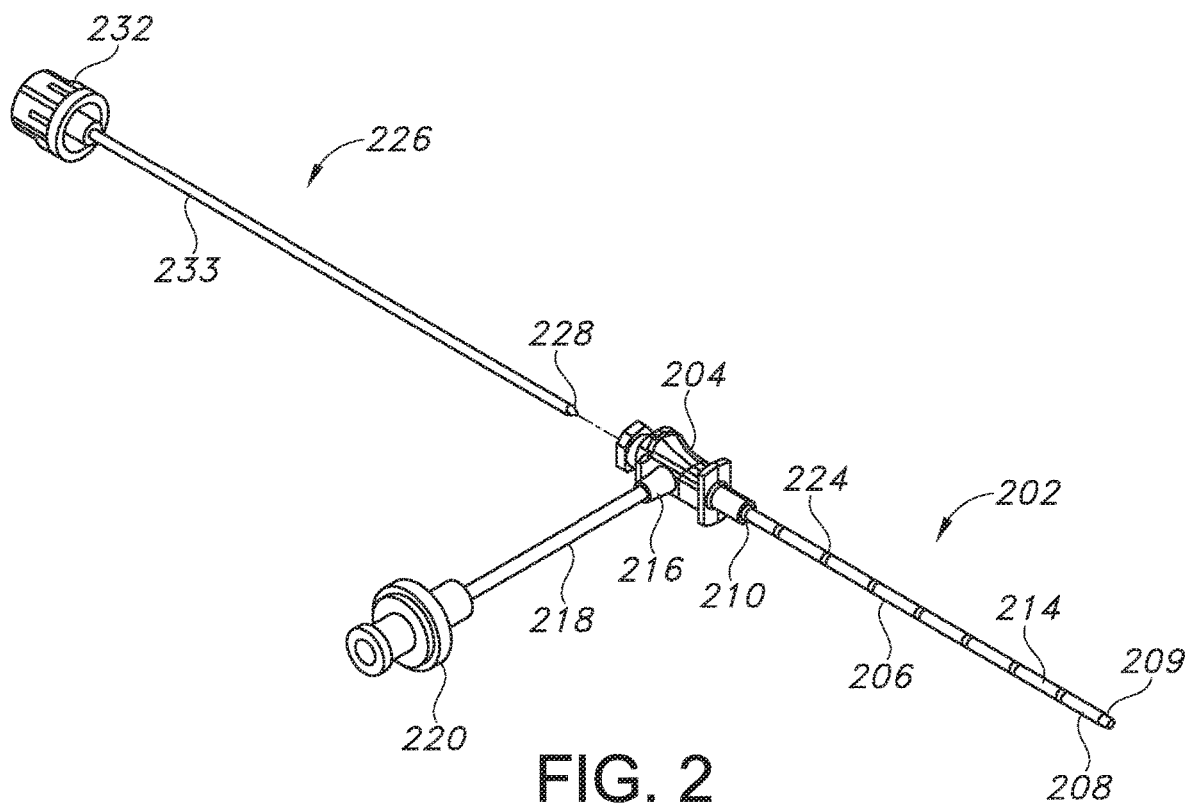
FIG. 2 is a perspective view of one embodiment of an introducer and stylet that can be used in the system of FIG. 1.
Figure 3:
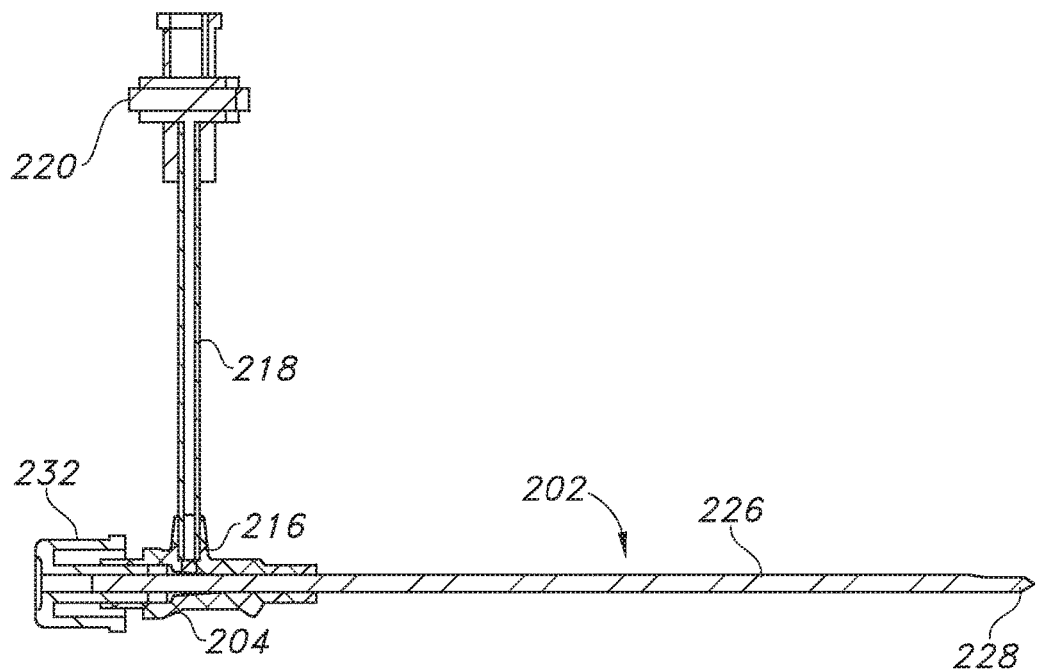
FIG. 3 is a longitudinal cross-section of the combined stylet and introducer of FIG. 2.

Referring to FIGS. 2 and 3, generally, the introducer 202 has a proximal end 210 configured with a hub 204 and a cannula 206 (defining an internal lumen) having a distal end 208. As understood in the art, the introducer 202 is operable to easily and securely couple with the RF probe assembly 106. For example, the proximal hub 204 is configured with a connector, such as a luer-lock connector, able to mate with the handle 180 of the RF probe assembly 106. The introducer cannula 206 is used to gain access to a tissue treatment site within a patient's body, wherein the elongate shaft 184 of the RF probe assembly 106 may be introduced to the treatment site through the longitudinal lumen of the introducer cannula 206.

Function of the stylet 226 is understood in the art. Generally, the stylet 226 includes a proximal hub 232 fixed to an elongate needle 233 having a beveled tip at the distal end 228 thereof. The elongate needle slides through the introducer 202 such that the stylet hub 232 connects to the introducer hub 204, for example via a luer-lock connection between the hubs 232 and 204, as depicted in FIG. 3. The distal end 228 of the stylet needle 233 extends past the distal end 208 of the introducer cannula 206 to facilitate insertion of the introducer cannula 206 into the patient's body at the treatment target site. Various forms of stylets 226 are well known in the art and the present invention is not limited to include only one specific form. Further, the stylet 226 may be operable to connect to a power source and may therefore form part of an electrical current impedance monitor.

Referring to FIGS. 2 and 3, the introducer 202 may include a fluid introduction port 216 in the proximal hub 204 that is in fluid communication with the proximal end 210 of the cannula 206. This port 216 may be defined at a ninety-degree angle relative to a longitudinal axis of the introducer 202, as depicted particularly in FIG. 3. A flexible or rigid fluid delivery tube 218 can be connected to the port 216, and a fitting 220 may be connected to the opposite end of the tube 218, wherein fluids such as saline or a local anesthesia can be injected into the target tissue via the fitting 220 and port 216 while the RF probe assembly 106 remains inserted in the introducer 202. The tube 218 may be fixed to the port 216 and the fitting 220 with a suitable medical grade adhesive. The fitting 220 may include a check valve that allows fluid to be injected into the fluid delivery port 216 through the fitting 220, for example with a syringe, while preventing backflow of fluid when the syringe is removed.

As discussed, the present invention encompasses a system for the application of RF energy 100 that includes an RF ablation probe system 200 (FIG. 1) for use in locating an RF probe assembly 106 at a target location within tissue to treat or manage pain in a patient. The system 200 includes the RF probe assembly 106, the introducer 202 discussed above, as well as the stylet 226 that is insertable through the proximal hub 204 and into the cannula 206. The characteristics and features of the introducer 202 and stylet 226 discussed above with respect to FIGS. 1-3 are applicable to the introducer 202 and stylet 26 that can be used in conjunction with the RF ablation probe system 200 discussed in more detail with respect to FIGS. 4-7.

Figure 4:
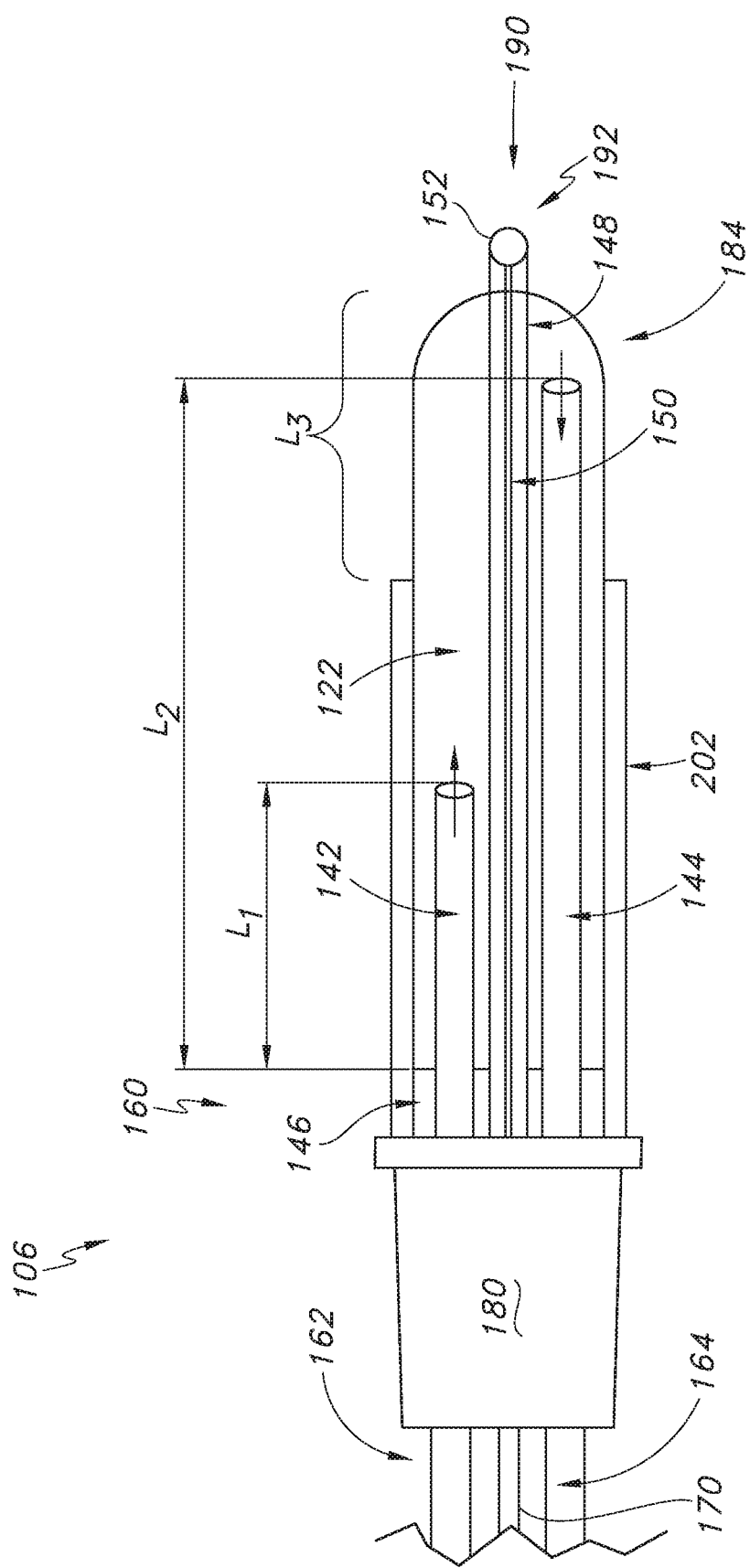
FIG. 4 is a diagram of one configuration of a probe assembly for forming a first lesion size using the system of FIG. 1.
Figure 5:
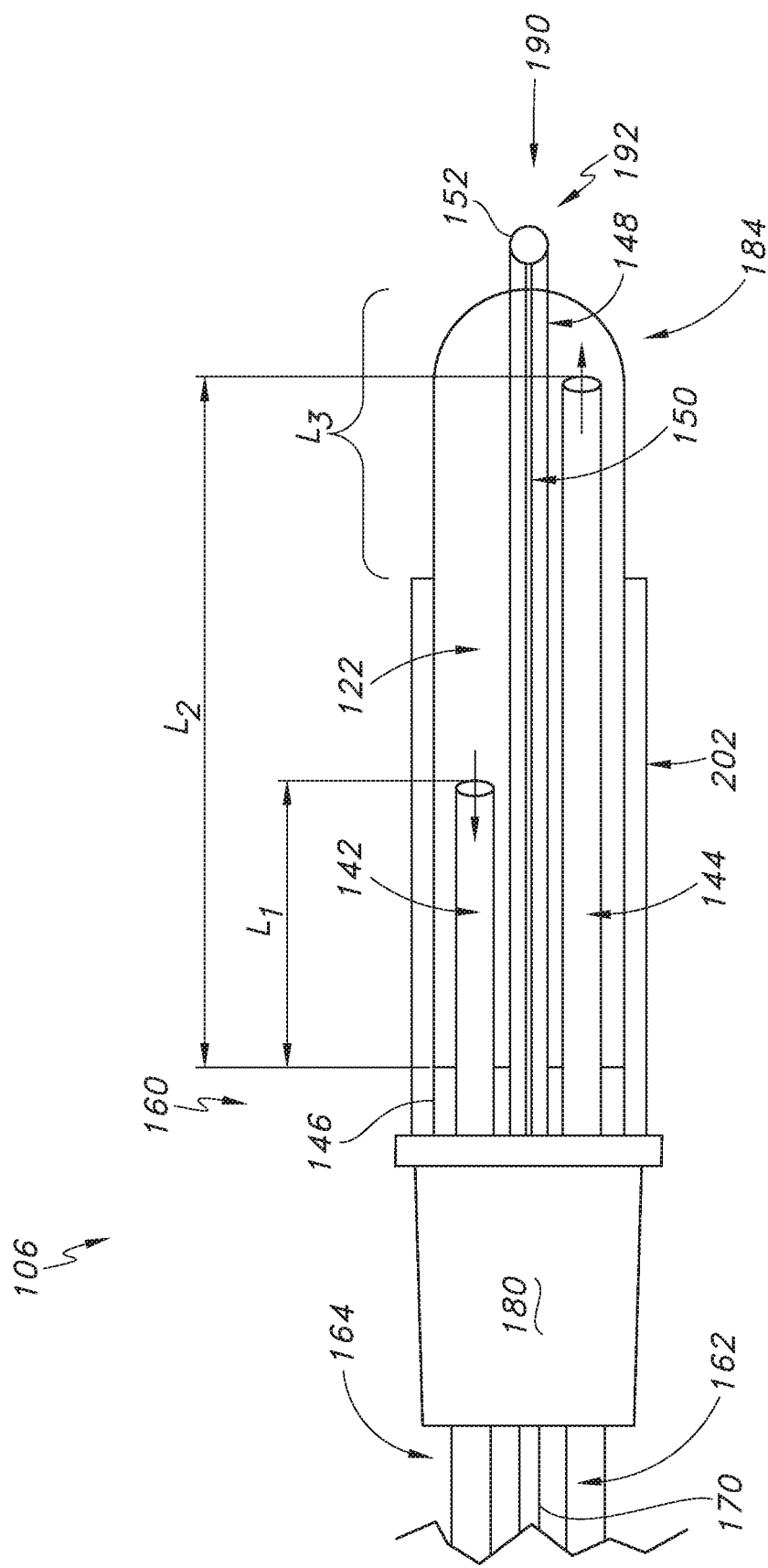
FIG. 5 is a diagram of another probe assembly for forming a second lesion size using the system of FIG. 1.
Figure 8:
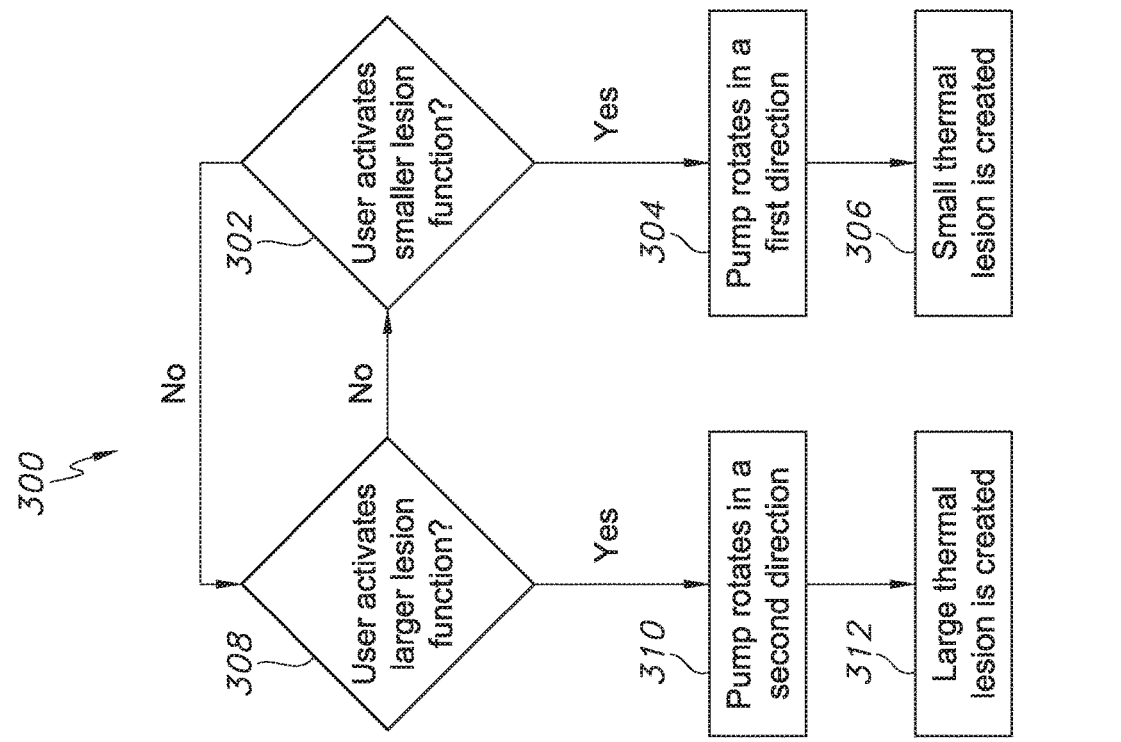
FIG. 8 is a schematic illustrating a method for determining whether to use the configuration of FIGS. 4 and 6 or the configuration of FIGS. 5 and 7 depending on the desired lesion size.

Referring to FIGS. 4-5, the RF ablation probe system 200 of the present invention is shown in a first configuration (FIG. 4) and a second configuration (FIG. 5). Regardless of the particular configuration that is selected during a particular procedure or during a particular part of a procedure as the case may be, the RF ablation probe system 200 can include a probe assembly 106 having a proximal region or end 160 including a handle 180 and a distal tip region 190 that can also be referred to as an active tip that includes an energy delivery device or conductive portion 192 for delivering energy to a target location within a patient's tissue located at or near the distal region. The distal tip region 190 can also include a thermocouple junction 152 for sensing the temperature of the active tip during an RF ablation procedure. Further, the probe assembly cable 170, the distal cooling fluid supply tube 162, and the distal cooling fluid return tube 164 discussed above with respect to FIG. 1 can be connected to the probe assembly 106 via the handle 180 at the proximal region or end 160 of the probe assembly 106.

Further, a single piece hollow elongate shaft or electrocap 184 can extend from the handle 180 to the distal tip region 190 of the probe assembly 106 to define an internal cavity 122. A hypodermic tube 148, such as a 28-gauge metal hypodermic tube, can extend concentrically through the center of internal cavity 122 of the hollow elongate shaft 184 and can penetrate the tip of the hollow elongate shaft 184 at the distal tip region 190 of the probe assembly. The hypodermic tube 148 can be circumferentially welded to the hollow elongate shaft 184 near the handle 180 of the probe assembly 106 forming a water tight and structurally strong bond at location 146. A wire 150, such as a constantan wire containing a copper/nickel alloy, can extend concentrically through the center of the hypodermic tube 148. In some embodiments, the wire 150 can be a 38-gauge solid core constantan wire. The wire 150 can be electrically insulated along its entire length expect at the distal tip region 190 of the probe assembly 106 where it is welded to the hypodermic tube 148 forming a dome-shaped thermocouple junction 152. Further, as shown, during an RF ablation procedure, the hollow elongate shaft 184 can be placed concentrically inside the introducer 202 that is electrically insulated along its entire length. The length of the introducer 202 is shorter than the length of the hollow elongate shaft 184, resulting in a section of the hollow elongate shaft 184 being electrically exposed, where the length of this section is known as the active tip length L3.

Referring still to FIGS. 4-5, two lengths of internal cooling fluid tubing are positioned inside the internal cavity 122 of the hollow elongate shaft 184 from the handle 180 towards the distal tip region 190. As shown, the first internal cooling fluid tube 142 can have a length L1 that is shorter than a length L2 of the second internal cooling fluid tube 144. Further, the present inventor has found that by specifically controlling the ratio of the length L1 to the length L2 to fall within a certain percentage, the width, height, and surface area of a resulting lesion can be precisely controlled without having to adjust the active tip length L3 of the probe assembly 106, which results in a more efficient and more accurately controlled RF ablation procedure. In one particular embodiment, the length L1 of the first (shorter) internal cooling fluid tube 142 should have a length that is less than about 40% of the length L2 of the second (longer) internal cooling fluid tube 144. For instance, the length L1 should be from about 2.5% to about 40%, such as from about 5% to about 35%, such as from about 10% to about 30%, such as from about 15% to about 25% of the length L2.

More specifically, in a first flow direction configuration (e.g., configuration 1 as shown in FIG. 4), the shorter first internal cooling fluid tube 142 can serve as the inlet for the cooling fluid by virtue of being connected to the distal cooling fluid supply tube 162, and the longer second internal cooling fluid tube 144 can serve as the outlet for the cooling fluid by virtue of being connected to the distal cooling fluid return tube 164. Meanwhile, in a second flow direction configuration (e.g., configuration 2 as shown in FIG. 5, the longer second internal cooling fluid tube 144 can serve as the inlet for the cooling fluid by virtue of being connected to the distal cooling fluid supply tube 162, and the shorter first internal cooling fluid tube 142 can serve as the outlet for the cooling fluid by virtue of being connected to the distal cooling fluid return tube 164. In either configuration, a water tight barrier at location 146 can be formed at the proximal end 160 of the hollow elongate shaft 184 at the handle 180, thus allowing the cooling fluid to circulate within the internal cavity 122 prior to flowing out through the distal cooling fluid return tube 164. The overall length of the longer second internal cooling fluid tube 144 scales with the overall length of the hollow elongate shaft 184, regardless of the overall length, and the longer tubing is inserted almost completely into the hollow elongate shaft 184.

Figure 7:
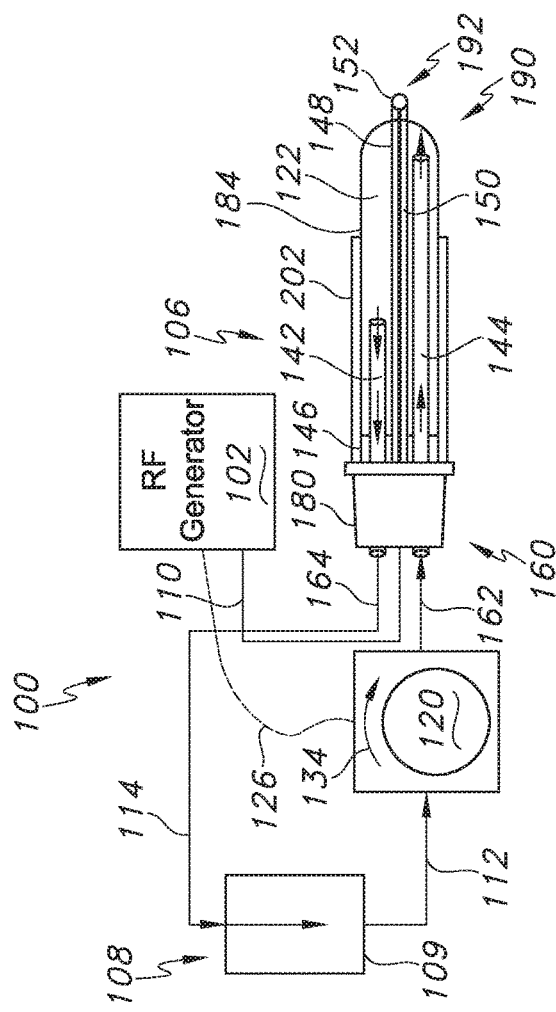
FIG. 7 is a diagram illustrating the arrangement of a pump and the probe assembly of FIG. 5.
Figure 6:
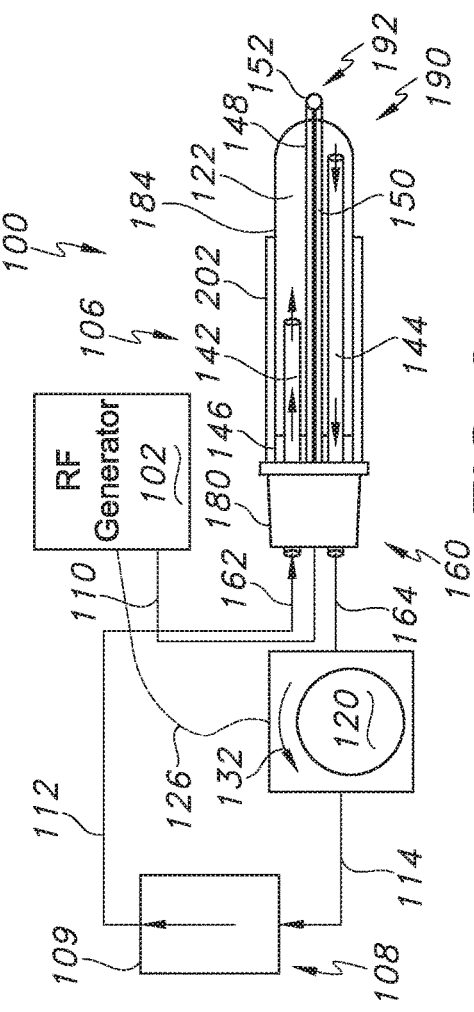
FIG. 6 is a diagram illustrating the arrangement of a pump and the probe assembly of FIG. 4.

Referring now to FIGS. 6-7, the ability to control the size of a lesion formed in a target location within tissue during a radiofrequency ablation procedure using the probe assembly with multiple configurations as described in FIGS. 4-5 is discussed in more detail. Specifically, the system 100 of the present invention contemplates the use of an RF generator 102 in conjunction with a cooling device 108 that utilizes a cooling fluid reservoir 109 in conjunction with a bidirectional pump assembly 120 located either upstream (FIG. 6) or downstream (FIG. 7) of the cooling fluid reservoir 109 that is capable of delivering cooling fluid to the probe assembly a first direction and an opposite second direction to control lesion size.

As shown in FIG. 6 and depending on instructions transmitted via a controller to the bidirectional pump assembly 120 via a signal 126 from, for instance, a user input such as a graphical user interface present on the RF generator 102, the bidirectional pump 120 is capable of pumping cooling fluid into the internal cavity 122 of the hollow elongate shaft 184 of the probe assembly 184 in a first direction 132 so that the cooling fluid enters the shorter first internal cooling fluid tube 142 and then travels toward the distal tip region 190 and into the longer second internal cooling fluid tube 144 to exit the probe assembly 106. In some embodiments and based upon the specific location of the pump assembly 120 in relation to the shorter first internal cooling fluid tube 142 and the longer second internal cooling fluid tube 144, the pump assembly 120 operates in a counterclockwise direction, although it is to be understood that depending on the particular arrangement of the system 100 components, the pump assembly 120 may operate in a clockwise direction in order to deliver cooling fluid to the shorter first internal cooling fluid tube 142, where the cooling fluid exits the probe assembly 106 via the longer second internal cooling fluid tube 144.

Meanwhile, as shown in FIG. 7 and also depending on instructions transmitted to the bidirectional pump assembly 120 via a signal 126 from, for instance, a graphical user interface present on the RF generator 102, the bidirectional pump 120 is capable of pumping cooling fluid into the internal cavity 122 of the hollow elongate shaft 184 of the probe assembly 184 in a second, opposite direction 134 so that the cooling fluid enters the longer second internal cooling fluid tube 144 first and then travels toward the proximal region 160 and into the shorter first internal cooling fluid tube 142 to exit the probe assembly 106. In some embodiments and based upon the specific location of the pump assembly 120 in relation to the shorter first internal cooling fluid tube 142 and the longer second internal cooling fluid tube 144, the pump assembly 120 operates in a clockwise direction, although it is to be understood that depending on the particular arrangement of the system 100 components, the pump assembly 120 may operate in a counterclockwise direction in order to initially deliver cooling fluid to the longer second internal cooling fluid tube 144, where the cooling fluid exits the probe assembly 106 via the shorter first internal cooling fluid tube 142.

Thus, the system 100 of the present invention contemplates creation of a lesion having a predetermined size at a target location within tissue via the delivery of cooling fluid in a particular direction via the bidirectional pump assembly 120. Further, although the configuration of FIG. 6 where the bidirectional pump assembly 120 is located upstream from the cooling fluid reservoir 109 results in the formation of smaller lesion since the cooling fluid enters the shorter first internal cooling fluid tube 142 before the longer second internal cooling fluid tube 144, and the configuration of FIG. 7 where the bidirectional pump assembly 120 is located downstream from the cooling fluid reservoir 109 results in the formation of a larger lesion since the cooling fluid inters the longer second internal cooling fluid tube 144 before the shorter first internal cooling fluid tube 142, it is to be understood that the location of the bidirectional pump assembly 120 in relation to the cooling fluid reservoir 109 can be reversed in some embodiments. For instance, in FIG. 6, the bidirectional pump assembly 120 could be located downstream of the cooling fluid reservoir 109 to create a smaller lesion, while in FIG. 7, the bidirectional pump assembly 120 could be located upstream of the cooling fluid reservoir so long as the cooling fluid enters the appropriate internal cooling fluid tube 142 or 144 first based on whether a smaller lesion or a larger lesion, respectively, is desired.

The present invention also encompasses various method embodiments for use energy delivery system 100 and RF ablation probe system 200 as described and enabled above. Specifically, and referring to FIG. 8, a method 300 for delivery of cooled radiofrequency energy to a target location of tissue can include a user responding to prompts on a graphical user interface (not shown) of an RF generator 102, where, in step 302, the user is asked if the user wants to activate a smaller lesion function. If the answer is yes, then in step 304, the pump assembly 120 is instructed to operate in a first direction, after which a small thermal lesion is created in step 306. Meanwhile, if the answer is no in step 302, then the user is asked if the user wants to activate a larger lesion function in step 308. If the answer is yes, then in step 308, the pump assembly 120 is instructed to operate in a second direction that is opposite from the first direction, after which a large thermal lesion is created in step 312. Further, although the method 300 described above describes inquiring about the activation of a smaller lesion function first, the method 300 also contemplates asking the user if the user wants to activate a larger lesion function first, or the user can be asked which lesion size should be formed, and the user can select the smaller lesion function or the larger lesion function. In one particular embodiment, the user can either activate the smaller lesion function or the larger lesion function. If the smaller lesion function is activated, the RF generator 102 instructs the pump assembly 120 to rotate in the counter-clockwise direction, pumping cooling fluid from the reservoir through the shorter first internal cooling fluid tube 142 as the inlet, where the fluid is returned to the reservoir of the cooling device 108 through the longer second internal cooling fluid tube 144 (flow configuration 1) resulting in a small thermal lesion. Conversely, if the larger lesion function is activated, the RF generator 102 instructs the pump assembly 120 to rotate in the clockwise direction, pumping cooling fluid from the reservoir of the cooling device 108 through the longer second cooling fluid tube 144 as the inlet, where the fluid is returned to the reservoir of the cooling device 108 through the shorter first internal cooling fluid tube 142 (flow configuration 2), resulting in a large thermal.

The present invention may be better understood by reference to the following example.

Example

Figure 9:
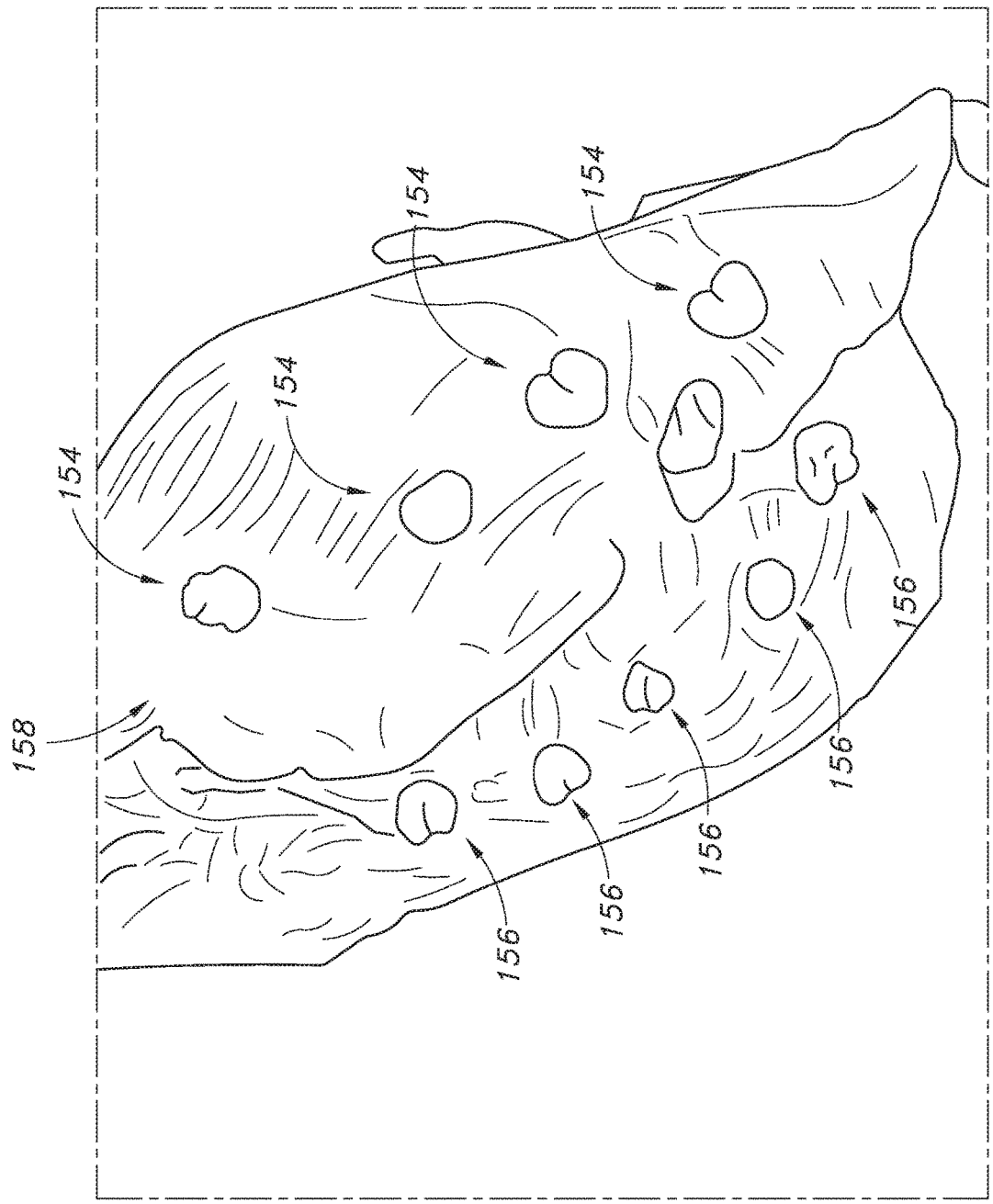
FIG. 9 illustrates the difference in lesion size based on whether the configuration of FIGS. 4 and 6 or the configuration of FIGS. 5 and 7 is utilized.

The ability to control lesion size based on directional cooling flow as contemplated by the present invention was demonstrated on a sample of tissue 158, as represented by raw chicken breast in this Example. In configuration 1, the inlet cooling fluid flow was through a section of shorter internal cooling fluid tubing having a length of 25 millimeters inside a probe having a length of 100 millimeters, while the outlet cooling fluid flow was through longer internal cooling fluid tubing having a length of 100 millimeters, where the shorter fluid tubing was 25% of the length of the longer fluid tubing. In configuration 2, the inlet cooling fluid flow was through the longer internal cooling fluid tubing having a length of 100 millimeters, while the outlet cooling fluid flow was through the shorter internal cooling fluid tubing having a length of 25 millimeters. As shown in Table 1 below, the lesion height and width were increased for configuration 2 compared to configuration 1, demonstrating that using the longer internal cooling fluid tubing for the inlet tubing and the shorter internal cooling tubing for the outlet tubing results in a larger lesion having an increased length/height and width. In addition, FIG. 9 shows that lesions formed in configuration 1, as represented by reference numeral 156, were generally smaller in overall surface area compared to lesions formed in configuration 2, as represented by reference numeral 154. In other words, the lesions 154 formed by configuration 2 were generally larger in overall surface area compared to lesions 156 formed in configuration 1.

TABLE 1

Lesion Height and Width Comparison:
Configuration 1 vs. Configuration 2

| Sample | Lesion Height (mm) | Lesion Width (mm) |
| --- | --- | --- |
| Configuration 1, Trial 1 | 8.43 | 9.29 |
| Configuration 1, Trial 2 | 10.53 | 11.69 |
| Configuration 1, Trial 3 | 7.80 | 7.85 |
| Configuration 1, Trial 4 | 9.00 | 10.33 |
| Configuration 1, Trial 5 | 8.25 | 9.82 |
| Configuration 1, Average | 8.80 | 9.79 |
| Configuration 1, Standard Deviation | 1.06 | 1.41 |
| Configuration 2, Trial 1 | 10.25 | 12.09 |
| Configuration 2, Trial 2 | 10.07 | 11.52 |
| Configuration 2, Trial 3 | 11.35 | 13.74 |
| Configuration 2, Trial 4 | 11.07 | 12.69 |
| Configuration 2, Trial 5 | 10.43 | 12.05 |
| Configuration 2, Average | 10.63 | 12.42 |
| Configuration 2, Standard Deviation | 0.55 | 0.85 |

Figure 11:
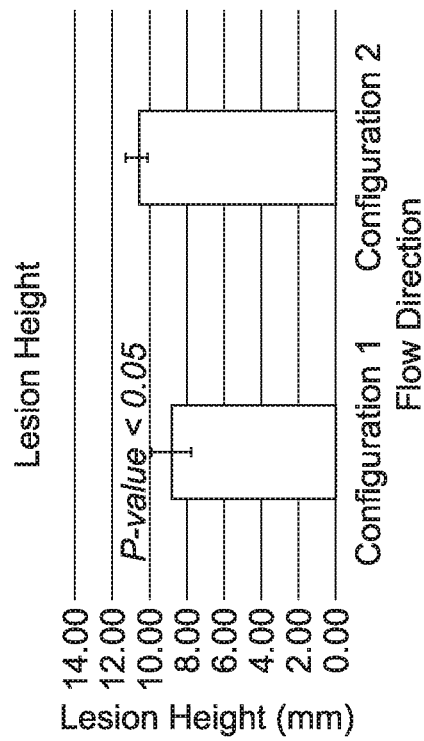
FIG. 11 is a bar graph illustrating the difference in lesion height based on whether the configuration of FIGS. 4 and 6 or the configuration of FIGS. 5 and 7 is utilized.
Figure 10:
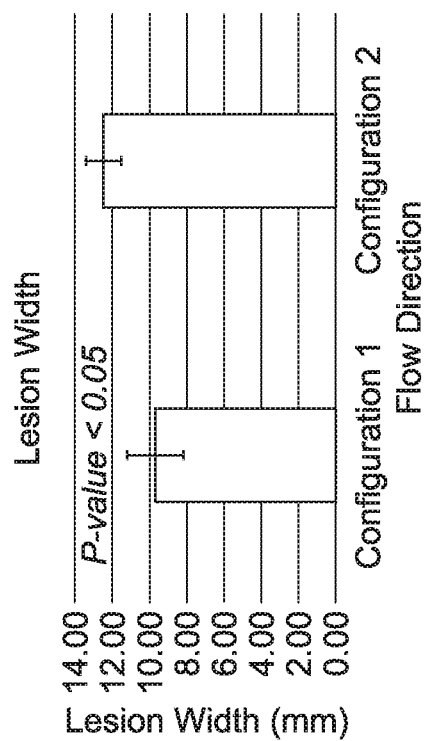
FIG. 10 is a bar graph illustrating the difference in lesion width based on whether the configuration of FIGS. 4 and 6 or the configuration of FIGS. 5 and 7 is utilized.

Referencing the bar graphs of FIGS. 10-11, ex-vivo thermal lesions were created in chicken breast using the same probe with a configuration 1 flow direction and a configuration 2 flow direction. The bar graph in FIG. 10 compares the difference in lesion width between configuration 1 and configuration 2. This graph indicates that configuration 2 creates a larger on average lesion width than configuration 1, the difference in width being statistically significant. The bar graph in FIG. 11 compares the difference in lesion height between configuration 1 and configuration 2. This graph indicates that configuration 2 creates a larger on average lesion height than configuration 1, the difference in height also being statistically significant. This data suggests that with the same probe, configuration 2 flow direction (e.g., where the inlet cooling fluid flows through the longer length of internal cooling fluid tubing inside the probe) creates a larger overall lesion than configuration 1 flow direction (e.g., where the inlet cooling fluid flows through the shorter internal cooling fluid tubing inside the probe).

The underlying mechanism of this effect is likely due to differences in heat transfer efficiencies. In configuration 1, the cooling fluid inlet through the shorter fluid tubing allows the fluid to exit into the hollow elongate shaft/electrocap internal cavity closer its proximal end. When the fluid exits, it transitions into a much larger cross-sectional area, resulting in a significant reduction in flow velocity and increase in transient time, which, in turn, allows for increased heat transfer from the warmer surrounding to the cooler cooling fluid. By the time the cooling fluid reaches the active tip, sufficient cooling efficiency is lost to result in a reduced cooling effect on the thermocouple and in response a decreased application of RF energy from the generator. Meanwhile, in configuration 2, the cooling fluid inlet through the longer fluid tubing can maintain high flow velocity until it reaches the distal tip, thus preserving the cooling efficiency and allowing the generator to apply greater amounts of RF energy.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A cooled radiofrequency ablation system comprising: a probe assembly comprising a single piece hollow elongated shaft extending from a handle at a proximal end of the probe assembly to a distal tip region of the probe assembly, the single piece hollow elongate shaft defining an internal cavity having a first internal cooling fluid tube and a second internal cooling fluid tube positioned therein, the first internal cooling fluid tube extending a first distance from the handle and the second internal cooling fluid tube extending a second distance from the handle, the second distance being greater than the first distance, the distal tip region comprising a conductive portion for delivering energy to a target location within a tissue; a radiofrequency generator for delivering energy to the target location via the conductive portion of the distal tip region of the probe assembly; a cooling device including a cooling fluid reservoir and a bidirectional pump assembly operable to circulate a cooling fluid through probe assembly; and a controller configured to selectively operate the bidirectional pump in a first mode or a second mode responsive to a user selection and in conjunction with the radiofrequency generator delivering energy, the first mode corresponding to the creation of a first size of lesion and the second mode corresponding to the creation of a second size of lesion that is larger than the first size of lesion, wherein: in the first mode, the bidirectional pump rotates in a first direction to transfer the cooling fluid from the cooling fluid reservoir, through the first internal cooling fluid tube, into the internal cavity, through the second internal cooling fluid tube, and back to the cooling fluid reservoir; and in the second mode, the bidirectional pump rotates in a second direction to transfer the cooling fluid from the cooling fluid reservoir, through the second internal cooling fluid tube, into the internal cavity, through the first internal cooling fluid tube, and back to the cooling fluid reservoir.

2. The cooled radiofrequency ablation system of claim 1, wherein the first distance is less than 40% of the second distance.

3. The cooled radiofrequency ablation system of claim 1, wherein the first distance is between 5% and 35% of the second distance.

4. The cooled radiofrequency ablation system of claim 1, wherein the bidirectional pump assembly is located upstream from the cooling fluid reservoir in the first direction and downstream from the cooling fluid reservoir in the second direction.

5. The cooled radiofrequency ablation system of claim 1, further comprising an introducer including a proximal end having a hub and a cannula extending from the hub and having a distal end.

6. The cooled radiofrequency ablation system of claim 5, further comprising a stylet insertable through the hub and into the cannula of the introducer, wherein the stylet comprises a tissue-piercing distal end that extends from the distal end of the cannula when the stylet is inserted into the introducer.

7. The cooled radiofrequency ablation system of claim 5, wherein the introducer electrically insulates the proximal end of the probe assembly when the probe assembly is inserted into the cannula.

8. The cooled radiofrequency ablation system of claim 1, wherein the bidirectional pump assembly is located downstream from the cooling fluid reservoir in the first direction and upstream from the cooling fluid reservoir in the second direction.

9. The cooled radiofrequency ablation system of claim 1, wherein the cooling fluid maintains a greater cooling efficiency when entering the internal cavity in the second mode than in the first mode, thereby allowing the second size of lesion to be larger than the first size of lesion.

10. The cooled radiofrequency ablation system of claim 9, wherein the radiofrequency generator is configured to deliver a greater amount of radiofrequency energy to the target location in the second mode versus the first mode due to the greater cooling efficiency of the cooling fluid.

11. A cooled radiofrequency ablation probe assembly for delivering energy to a target location within tissue, the cooled radiofrequency ablation probe assembly comprising: a proximal region; a single piece hollow elongated shaft extending from the proximal region to a distal tip region of the cooled radiofrequency ablation probe assembly, the single piece hollow elongated shaft defining an internal cavity having a first internal cooling fluid tube and a second internal cooling fluid tube positioned inside the internal cavity, the first internal cooling fluid tube extending a first distance from the proximal region and the second internal cooling fluid tube extending a second distance from the proximal region, the second distance being greater than the first distance; the distal tip region including a conductive portion for delivering energy to the target location; and a controller configured to selectively operate, responsive to a user selection, a bidirectional pump in a first mode or a second mode to provide cooling while energy is delivered via the conductive portion, wherein: the bidirectional pump is configured to transfer a cooling fluid in a first direction when operating in the first mode and in a second direction when operating in the second mode; in the first mode, the bidirectional pump rotates in the first direction to transfer the cooling fluid from an external cooling fluid reservoir, through the first internal cooling fluid tube, into the internal cavity, through the second internal cooling fluid tube, and back to the external cooling fluid reservoir; in the second mode, the bidirectional pump rotates in the second direction to transfer the cooling fluid from the external cooling fluid reservoir, through the second internal cooling fluid tube, into the internal cavity, through the first internal cooling fluid tube, and back to the external cooling fluid reservoir; and in the first mode, the cooled radiofrequency ablation probe assembly generates a first size of lesion that is smaller than a second size of lesion generated by the second mode of operation.

12. The cooled radiofrequency ablation probe of claim 11, wherein the first distance is less than 40% of the second distance.

13. The cooled radiofrequency ablation probe of claim 11, wherein the first distance is between 5% and 35% of the second distance.

14. A cooled radiofrequency ablation probe assembly for delivering energy to a target location within tissue, the cooled radiofrequency ablation probe assembly comprising: a proximal region; a hollow elongated shaft that is at least partially flexible, the hollow elongated shaft extending from the proximal region to a distal tip region of the cooled radiofrequency ablation probe assembly, the hollow elongated shaft defining an internal cavity having a first internal cooling fluid tube and a second internal cooling fluid tube positioned inside the internal cavity, the first internal cooling fluid tube extending a first distance from the proximal region and the second internal cooling fluid tube extending a second distance from the proximal region, the second distance being greater than the first distance; the distal tip region including a conductive portion for delivering energy to the target location; and a controller configured to selectively operate, responsive to a user selection, a bidirectional pump in a first mode or a second mode to provide cooling while energy is delivered via the conductive portion, wherein: the bidirectional pump is configured to transfer a cooling fluid in a first direction when operating in the first mode and in a second direction when operating in the second mode; in the first mode, the bidirectional pump rotates in the first direction to transfer the cooling fluid from an external cooling fluid reservoir, through the first internal cooling fluid tube, into the internal cavity, through the second internal cooling fluid tube, and back to the external cooling fluid reservoir; in the second mode, the bidirectional pump rotates in the second direction to transfer the cooling fluid from the external cooling fluid reservoir, through the second internal cooling fluid tube, into the internal cavity, through the first internal cooling fluid tube, and back to the external cooling fluid reservoir; and in the first mode, the cooled radiofrequency ablation probe assembly generates a first size of lesion that is smaller than a second size of lesion generated by the second mode of operation.

15. The cooled radiofrequency ablation probe assembly of claim 14, wherein at least a surface of the hollow elongated shaft is insulated.

* * * * *